(12) United States Patent
Honda et al.

(10) Patent No.: US 8,041,422 B2
(45) Date of Patent: Oct. 18, 2011

(54) IN-BODY INFORMATION ACQUIRING APPARATUS AND POWER-SUPPLY CIRCUIT

(75) Inventors: Takemitsu Honda, Tokyo (JP); Toshiaki Shigemori, Tokyo (JP); Seiichiro Kimoto, Tokyo (JP); Ayako Nagase, Tokyo (JP); Katsuyoshi Sasagawa, Tokyo (JP); Hatsuo Shimizu, Tokyo (JP); Tetsuo Minai, Tokyo (JP); Tsutomu Nakamura, Tokyo (JP); Hiroshi Suzushima, Tokyo (JP); Noriyuki Fujimori, Tokyo (JP); Tatsuya Orihara, Tokyo (JP); Katsuya Suzuki, Tokyo (JP); Masayuki Hashimoto, Tokyo (JP); Kazutaka Nakatsuchi, Tokyo (JP)

(73) Assignee: Olympus Corporation, Tokyo (JP)

(*) Notice: Subject to any disclaimer, the term of this patent is extended or adjusted under 35 U.S.C. 154(b) by 630 days.

(21) Appl. No.: 12/172,737

(22) Filed: Jul. 14, 2008

(65) Prior Publication Data
US 2008/0278970 A1 Nov. 13, 2008

Related U.S. Application Data

(62) Division of application No. 10/814,078, filed on Mar. 31, 2004, now abandoned.

(30) Foreign Application Priority Data

Apr. 1, 2003 (JP) .................................. 2003-098594

(51) Int. Cl.
 *A61N 1/30* (2006.01)
(52) U.S. Cl. .......................................................... 604/20
(58) Field of Classification Search .................. 323/222, 323/224, 282–285; 320/114, 120, 104, 150; 604/20, 501, 503; 607/1–7, 50, 63, 64, 75, 607/152
See application file for complete search history.

(56) References Cited

U.S. PATENT DOCUMENTS

| 688,009 | A |   | 12/1901 | Siegel et al. |
|---|---|---|---|---|
| 4,101,787 | A |   | 7/1978 | Vail |
| 4,297,590 | A |   | 10/1981 | Vail |
| 5,519,261 | A |   | 5/1996 | Stewart |
| 5,919,211 | A | * | 7/1999 | Adams .............................. 607/5 |
| 5,956,241 | A |   | 9/1999 | LoCacsio |
| 5,982,157 | A | * | 11/1999 | Wattenhofer et al. ......... 323/222 |
| 5,983,133 | A | * | 11/1999 | Garde et al. .................... 604/20 |
| 6,034,443 | A |   | 3/2000 | Oliemuller et al. |
| 6,087,709 | A |   | 7/2000 | Gan et al. |
| 6,181,067 | B1 |   | 1/2001 | Dalton |
| 6,268,711 | B1 |   | 7/2001 | Bearfield |
| 6,466,521 | B1 |   | 10/2002 | Mitaki |

(Continued)

FOREIGN PATENT DOCUMENTS

JP  9-149629  6/1997

(Continued)

*Primary Examiner* — Rajnikant Patel
(74) *Attorney, Agent, or Firm* — Scully, Scott, Murphy & Presser, P.C.

(57) ABSTRACT

An in-body information acquiring apparatus includes a function executing unit that realizes a predetermined function inside a body of a patient. A power-supply circuit includes a power unit that includes a cell and that outputs a first current and a first voltage; and a converter that converts the first current to a second current, which is a current required to operate the function executing unit for a predetermined time, and converts the first voltage to a second voltage, which is a voltage required to operate the function executing unit.

6 Claims, 10 Drawing Sheets

U.S. PATENT DOCUMENTS

| | | |
|---|---|---|
| 6,855,111 B2 | 2/2005 | Yokoi et al. |
| 6,936,003 B2 | 8/2005 | Iddan et al. |
| 7,116,352 B2 | 10/2006 | Yaron |
| 7,288,924 B2 * | 10/2007 | Trandafir et al. ............. 323/283 |
| 2004/0209161 A1 | 10/2004 | Dubac et al. |

FOREIGN PATENT DOCUMENTS

| | | |
|---|---|---|
| JP | 2002-508201 | 3/2002 |
| WO | WO 99-30610 | 6/1999 |

* cited by examiner

STEP-DOWN SWITCHING

MEASUREMENT PATTERN

IN-BODY INFORMATION ACQUIRING APPARATUS AND POWER-SUPPLY CIRCUIT

CROSS-REFERENCE TO RELATED APPLICATIONS

This application is a divisional application of U.S. patent application Ser. No. 10/814,078 filed on Mar. 31, 2004, which claims benefit from Japanese Patent Application No. 2003098594 filed on Apr. 1, 2003 the entire contents of each of which are incorporated herein by reference.

BACKGROUND OF THE INVENTION

1) Field of the Invention

The present invention relates to an apparatus, such as a capsule endoscope, that acquires information about internal structure of a patient (hereinafter, "in-body information acquiring apparatus") and a power-supply circuit.

2) Description of the Related Art

A swallowable capsule endoscope for medical treatment that can be introduced into the abdominal cavity of a patient and that collects information about internal structure of the abdominal cavity by taking pictures has been known. Japanese Patent Application Laid-open Publication No. 2002-508201 discloses a capsule endoscope in which are inbuilt an illuminating unit, which includes a light emitting diode (LED) etc.; a solid-state image sensor, which includes a charged coupled device (CCD) or a CMOS (complementary metal-oxide semiconductor); and a power-supply unit, which includes a battery cell (hereinafter, "cell") that supplies power to the illuminating unit or the solid-state image sensor.

The capsule endoscope has to be small so that a patient can swallow it. Thus, there is a great limitation on the size of the capsule endoscope and there is much greater limitation on the size of the cell of the capsule endoscope.

Moreover, since the capsule endoscope is required to operate stably, the cell has to be capable of supplying a stable predetermined voltage.

Since it is almost impossible to reuse the capsule, it is desirable that the capsule endoscope is cheap. To suppress the cost, one approach is to use the cells that are available in the market and not go for custom-made cells. Button cells that are used in wrist watches, portable games, thermometers etc. may be used in the capsule endoscopes; however, only limited types of such cells are available in the market and to choose a cell that satisfies the requirements of size, shape, life, output level etc. for use in the capsule endoscope is a difficult task.

SUMMARY OF THE INVENTION

It is an object of the present invention to provide a power-supply circuit that is low cost, compact, and that can be suitably used in an in-body information acquiring apparatus.

A power-supply circuit for an in-body information acquiring apparatus, the min-body information acquiring apparatus having a function executing unit that realizes a predetermined function inside a body of a patient, according to an aspect of the present invention, includes a power unit that includes a cell and that outputs a first current and a first voltage; and a converter that converts the first current to a second current, which is a current required to operate the function executing unit for a predetermined time, and converts the first voltage to a second voltage, which is a voltage required to operate the function executing unit.

A power-supply circuit for an in-body information acquiring apparatus, the in-body information acquiring apparatus having a function executing unit that realizes a predetermined function inside a body of a patient, according to another aspect of the present invention, includes a power unit that includes a first power unit that includes a cell that outputs a first current and a first voltage and a second power unit that includes a cell and that outputs a second current and a second voltage; and a switch that selectively connects any one of the first power unit and the second power unit to the function executing unit for a predetermined period so as to convert the first current or the second current to a third current, which is a current required to operate the function executing unit predetermined time, and converts the first voltage or the second voltage to a third voltage, which is a voltage required to operate the function executing unit.

An in-body information acquiring apparatus according to still another aspect of the present invention includes a function executing unit that realizes a predetermined function inside a body of a patient; a power unit that includes a cell and that outputs a first current and a first voltage; and a converter that converts the first current to a second current, which is a current required to operate the function executing unit for a predetermined time, and converts the first voltage to a second voltage, which is a voltage required to operate the function executing unit.

An in-body information acquiring apparatus according to still another aspect of the present invention includes a function executing unit that realizes a predetermined function inside a body of a patient; a power unit that includes a first power unit that includes a cell that outputs a first current and a first voltage; and a second power unit that includes a cell and that outputs a second current and a second voltage; and a switch that selectively connects any one of the first power unit and the second power unit to the function executing unit for a predetermined period so as to convert the first current or the second current to a third current, which is a current required to operate the function executing unit predetermined time, and converts the first voltage or the second voltage to a third voltage, which is a voltage required to operate the function executing unit.

The other objects, features, and advantages of the present invention are specifically set forth in or will become apparent from the following detailed description of the invention when read in conjunction with the accompanying drawings.

BRIEF DESCRIPTION OF THE DRAWINGS

FIG. 9A is a first example and FIG. 9B is a second example.

FIG. 12A illustrates the measurement pattern and FIG. 12A illustrates electrical discharge characteristics for the measurement pattern.

DETAILED DESCRIPTION

Exemplary embodiments of an in-body information acquiring apparatus and a power-supply circuit for the in-body information acquiring apparatus are explained below while referring to the accompanying drawings.

Figure 13:
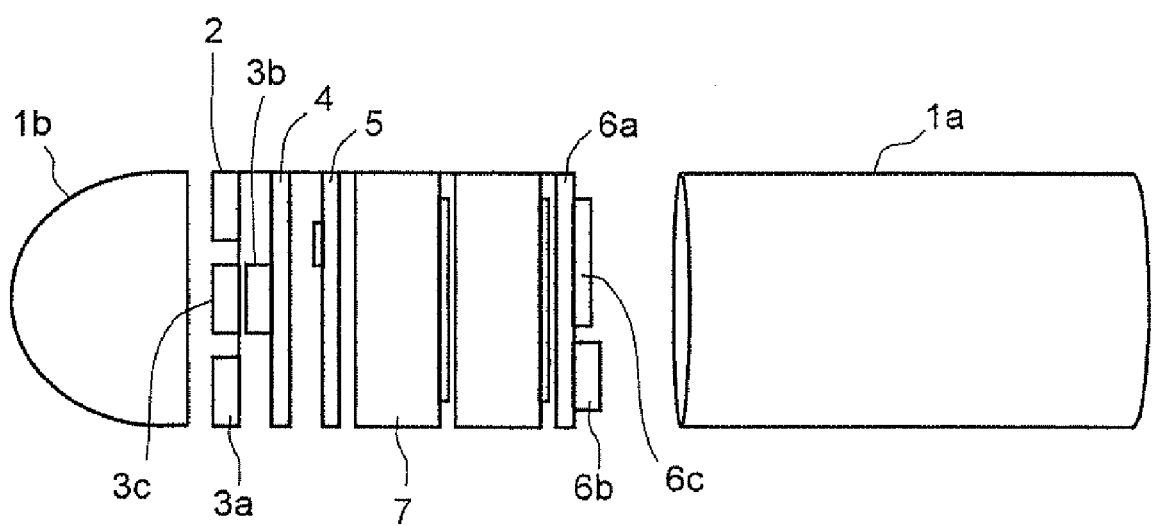
FIG. 13 is a schematic of an in-body information acquiring apparatus in which the power-supply circuit according to the present invention is used.

FIG. 13 is a schematic of an in-body information acquiring apparatus in which a power-supply circuit according to the present invention is used.

A reference numeral 1a denotes a case and 1b denotes a transparent dome that is fixed to the case 1a. An internal harness 2 in which various components are mounted is accommodated in the case 1a and the transparent dome 1b. The internal harness 2 includes an illuminating unit 3a, a solid-state image sensor 3b, an object lens 3c, a power-supply substrate 5, an antenna 6b, and a voltage controlled oscillator (VCO) 6c, The illuminating unit 3a includes an LED. The solid-state image sensor 3b is arranged on an imaging substrate 4 and includes a CCD. The solid-state image sensor 3b takes images, through the transparent dome 1b, of a region that is illuminated by the illuminating unit 3a. The object lens 3c is installed between the solid-state image sensor 3b and the transparent dome 1b. The power-supply substrate 5 includes a power-supply circuit that uses a cell 7 as a power supply. The antenna 6b is provided on a wireless substrate 6a and is meant for wireless communication with outside. The parts such as the illuminating unit 3a, the solid-state image sensor 3b, the wireless substrate 6a, the VCO 6c correspond to a function executing unit, and the cell 7 correspond to a power unit of the present invention.

A silver-oxide button cell is used as the cell 7; because, the voltage and current outputs of the silver-oxide button cell are appropriate and stable and it has a low voltage drop and flat electrical discharge characteristics. A nominal voltage of the silver-oxide button cell is 1.55 volts (V).

Figure 1:
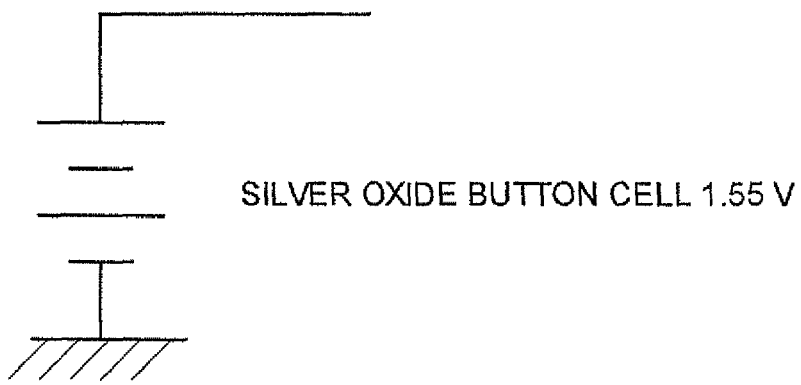
FIG. 1 is a circuit diagram in which two silver oxide button cells are connected in series.

The in-body information acquiring apparatus requires a voltage of 3.1 V and a current of a few milliamperes (mA) and it is expected to operate continuously for not less than eight hours. Precisely, the image sensor, i.e., an IC of a CMOS, requires 3.1 V. The voltage of 3.1 V can be obtained by connecting two silver-oxide button cells in series as shown in FIG. 1. A silver-oxide button cell that has a small diameter, i.e., less than 10 mm, and has a large electrical discharge i.e. about 50 mAh is used.

The nominal electrical discharge capacity of the silver-oxide button cell according to specifications (of the manufacturer) is about 50 mAh. It means that, according to the specifications, if a minute current of 0.075 mA is flowing when a small amount of operating voltage like that in a case of a wrist watch cell is used, the silver-oxide button cell has a life mentioned in the specifications or close to that mentioned in the specifications, i.e. about 600 hours.

The only data that is published and is available about the life of the silver-oxide button cell is when a minute current (maximum 0.1 mA on an average) that is supposed to be used originally for the silver-oxide button cell. The life indicates a time period and current which the silver-oxide button cell is supposed to be used for. In other words, data regarding life of the cell when a high current like that in the in-body information acquiring apparatus flows has not been published at all. This is because there is a great difference between the current and the life that is required to be used in the in-body information acquiring apparatus and the actual current and the life of the silver-oxide button cell which is supposed to be used for. So far, there is no other product except the in-body information acquiring apparatus in which the silver-oxide button cell is used for a current that is extremely greater than the current the silver-oxide button cell is supposed to be used for originally.

The Inventors of the present invention confirmed with experiments that, when a high operating current of 5 mA is drawn from the silver-oxide button cell, as in the case of the in-body information acquiring apparatus, it does not last for the period (e.g., 50 mAh/5 mA=10 hours) that is calculated by the formula mentioned in the specifications.

Concretely, if an average current of 5 mA is drawn from a cell, the cells drain in about only four hours so that the life of the cells is almost only half of the requirement. If two sets of cells, each set cell including two cells connected in series as shown in FIG. 1, are connected in parallel, the cells can last for about eight hours. However, since most of the space in the in-body information acquiring apparatus is occupied by the cells, this assembly of cells is not suitable because there is no room left for other structure. For example, because the height of the SR41W cell is 3.6 mm, the total height of two cells will be 7.2 mm, and the total height four cells (two sets of two cells each) will be 14.4 mm. Thus, most of the space inside the in-body information acquiring apparatus shall be occupied by the cells.

Figure 2:
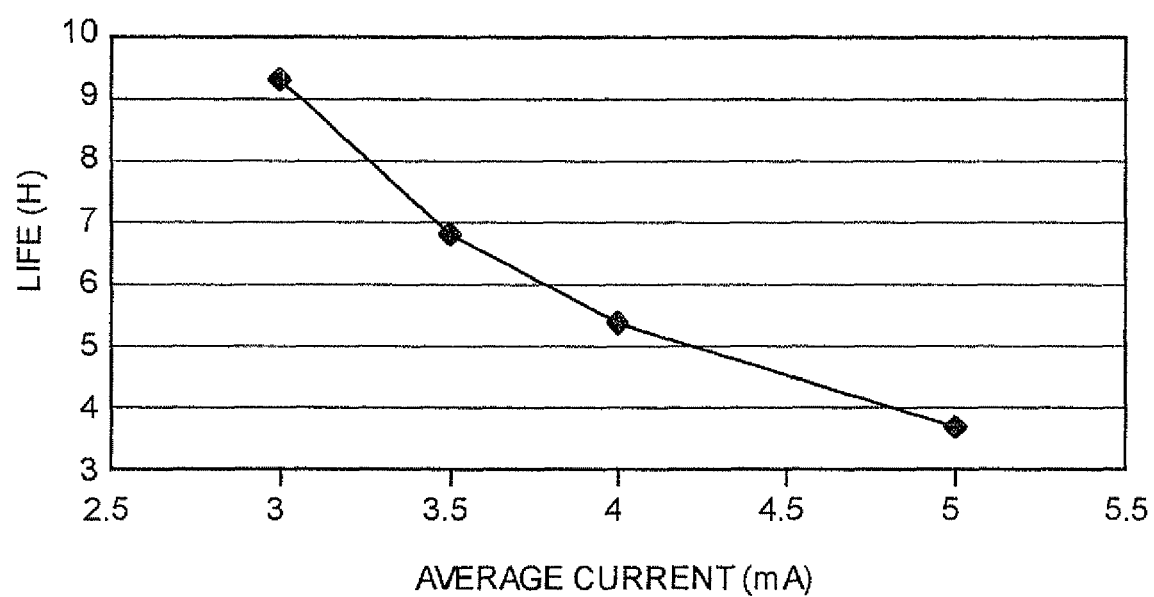
FIG. 2 is a graph of an average current output drawn from a silver-oxide button cell and the life of the silver-oxide button cell.

FIG. 2 is a graph of an average current output drawn from a silver-oxide button cell and the life of the silver-oxide button cell. It is clear from the graph that, the larger is the average current that is drawn from a cell, the lower is the efficiency compared to the nominal specifications value (45 mAh), in other words, the shorter is the life. Concretely, when the average current is 3 mA, the life is about nine hours, which corresponds to an efficiency of 27 mAh. When the average current is 3.5 mA, the life is about seven hours, which corresponds to an efficiency of 5 mAh. When the average current is 5 mA, the life is about four hours, which corresponds to about 20 mAh. Although the graph corresponds to the SR41W cell, almost similar graph is obtained for any silver-oxide button cell other than the SR41W cell.

The cell of the in-body information acquiring apparatus is required to last for not less than eight hours; therefore, if the silver-oxide button cell (SR41W) is to be used, it is necessary to control the average current drawn from each cell to less than 3.2 mA. If any other cell is to be used, then, it becomes necessary to obtain the characteristic of that cell, and decide how much current can be drawn from the cell so that the cell lasts for eight hours.

The present invention aims to provide a power-supply circuit that:
1) provides an output voltage of 3.1 V and an output average current of 5 mA, and
2) makes it possible to suppress a current drawn from each cell to a minimum so as to prolong the life of the cell.

Figure 3:
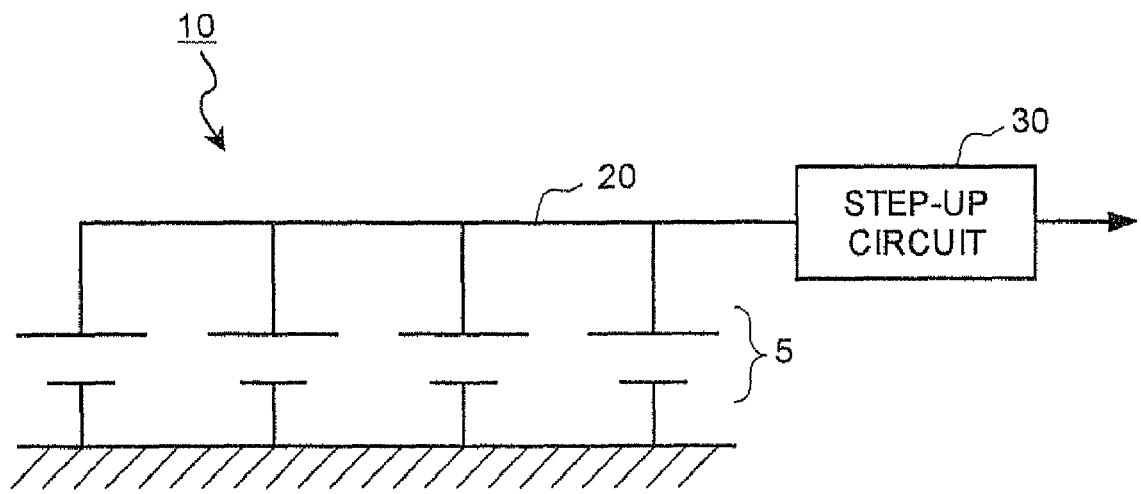
FIG. 3 is a circuit diagram of a power-supply circuit according to a first embodiment of the present invention.

FIG. 3 is a circuit diagram of a power-supply circuit 10 according to a first embodiment. The power-supply circuit 10 includes a power-supply unit 20 and a step-up circuit 30 as a power converting unit. The power-supply unit 20 includes four silver-oxide button cells 5 connected in parallel. The cells 5 are the SR726SW cells. The SR726SW cell has a lower capacity than that of the SR41W cell; however, the SR726SW cell is smaller than the SR41W cell. The electrical discharge capacity (nominal) of the SR726SW cell is 32 mAh, and the height is 2.6 mm. The diameter of the SR726SW cell is 7.9 mm which is same as that of the SR41W cell. Thus, the SR726SW cell is a cell suitable to be mounted in the in-body information acquiring apparatus.

The power-supply unit 20 outputs about 1.55 V. The step-up circuit 30 steps up, to double, the output voltage from the power-supply unit 20. Thus, the voltage output from the step-up circuit 30 is about 3.1 V. On the other hand, the step-up circuit 30 outputs a current that is half the value of current output from the power-supply unit 20. Therefore, if the power-supply circuit 10 is to output a current of 5 mA, it is necessary that the power-supply unit 20 outputs an average current of 10 mA. In the case of the SR726SW cell, it was confirmed with experiments that if a current of 2.5 mA is drawn from one cell, the cell last for required period (not less than eight hours). Therefore, four (10 mA/2.5 mA=4) cells 5 are connected in parallel in the power-supply unit 20.

The step-up circuit 30 may be a step-up switching regulator circuit or a charge pump. The step-up switching regulator circuit will now be explained while referring to FIGS. 4, 5A, and 5B.

The step-up switching regulator circuit is a power converting unit for achieving stable voltage and stable current with high conversion efficiency. The step-up switching regulator circuit includes a switch that is provided between an unstable power supply and a load. The power of the power supply is supplied to the load or is cut off by controlling ON/OFF of the switch. The power to be supplied to the load can be adjusted on average by repeating the ON-OFF operation at a high speed, thereby stabilizing the voltage and the current. The switch and the load are connected in parallel. A change in voltage by increasing or decreasing the current flowing through a coil, is used. The step-up switching regulator circuit is assembled with a feed-back circuit that compares the output voltage with a reference value and maintains it to a stable voltage.

Figure 4:
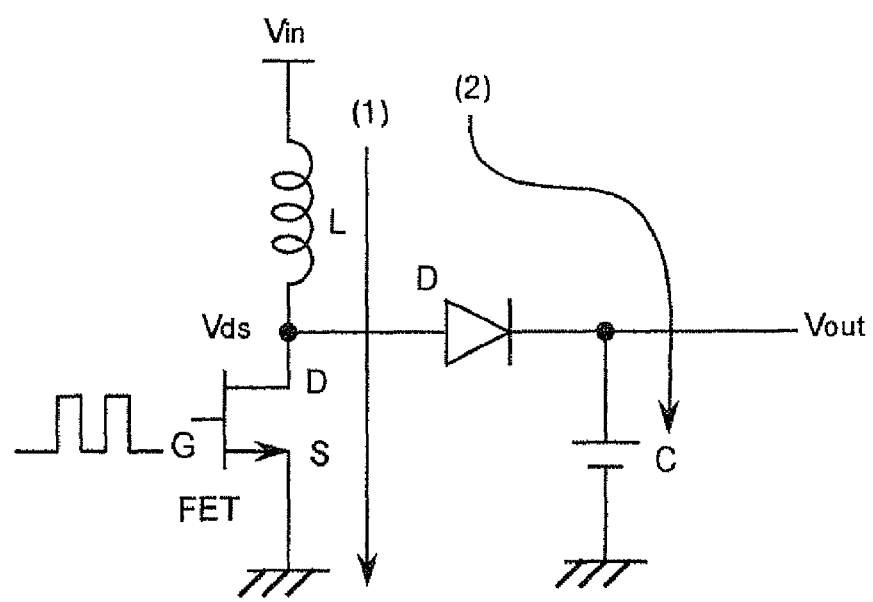
FIG. 4 is a circuit diagram of a step-up switching regulator circuit as an example of a step-up circuit in the power-supply circuit shown in FIG. 3.

FIG. 4 is an exemplary circuit diagram of the step-up switching regulator circuit. The step-up switching regulator circuit includes a field-effect transistor (FET) for switching, an inductor L with a time-lag of a first order, a condenser C, and a diode D. The diode D prevents backward current to prevent the electric charge that is stored in the condenser from leaking when the FET is put ON. However, since there is a voltage drop of 0.7 V in the diode D, if an anode of the diode is at a voltage less than 0.7 V with respect to the output voltage Vout, the condenser does not get charged.

Vds is the unstable power supply and the diode is the switch. The ON/OFF operation of the diode is due to an ON/OFF operation of the FET switch. To start with, when the FET is turned ON, the Vds gets short-circuited with the ground (GND) and a current starts flowing in the inductor L (see the arrow (1)). As the current starts flowing in the inductor L, counter electromotive force is developed in the inductor L. When FET is turned OFF, there is high impedance in the Vds and due to the counter electromotive force in the inductor L an electric potential of the Vds becomes Vin+counter electromotive force. If the potential of the Vds is not less than Vout+0.7 V, the current flows in a path indicated by the arrow (2). With such an operation, the step-up switching regulator circuit (i.e., the step-up circuit 30) converts current 10 mA and voltage 1.55V output from the power-supply unit 20 to current 5 mA and voltage 3.1 V.

Figure 5A:
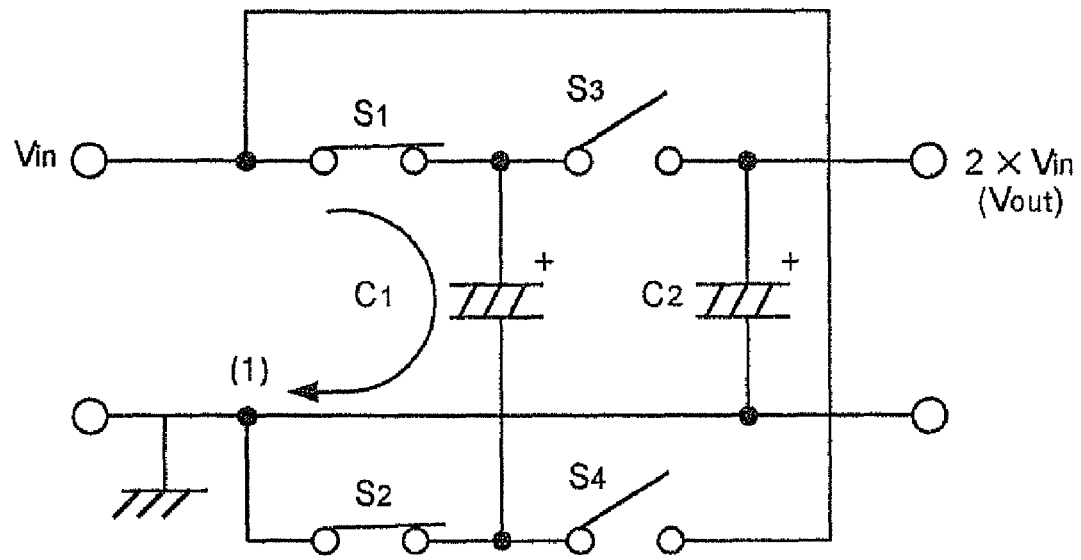
FIGS. 5A and 5B are circuit diagrams of a charge pump as an example of the step-up circuit.
Figure 5B:
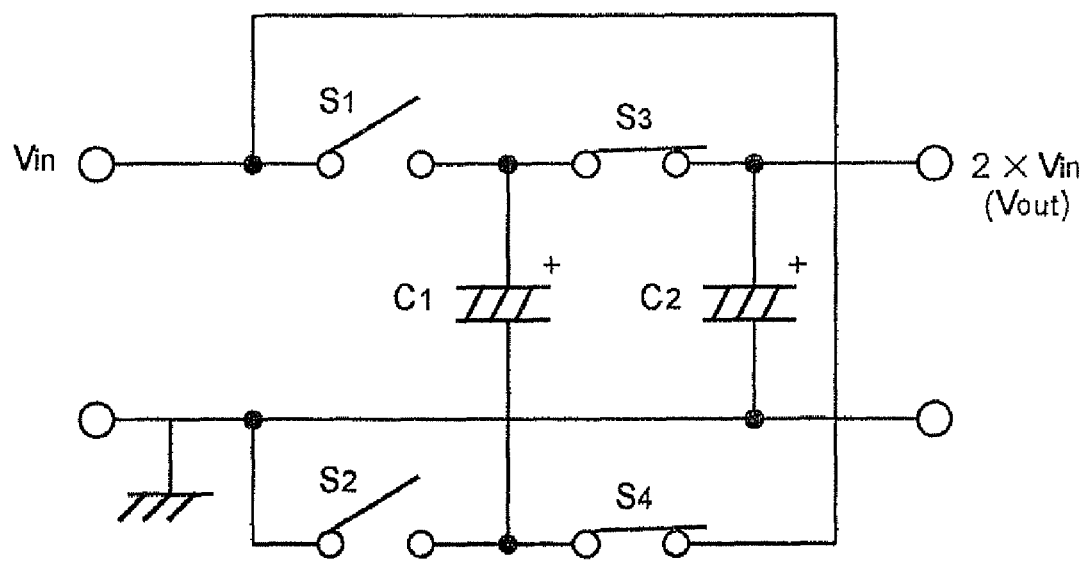
Figure 6:
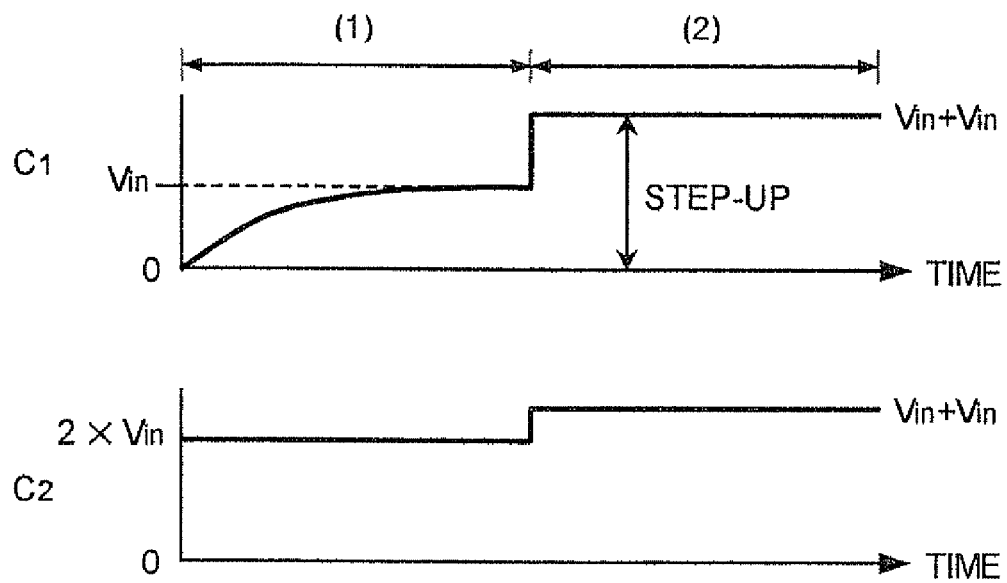
FIG. 6 is a time chart of an operation of the charge pump.

FIGS. 5A and 5B are circuit diagrams of the charge pump as an example of the step-up circuit. FIG. 6 is a time chart of an operation of the charge pump.

The charge pump operates in two steps: a first operation-step (see arrows (1) in FIGS. 5A and 6) and a second operation-step (see FIG. 5B and the arrow (2) in FIG. 6).

In the first operation-step, switches S1 and S2 are turned ON and a condenser C1 is charged quickly. As a result, electric potential V1 (1.55 V) is charged in the condenser C1.

In the second operation-step, the switches S1 and S2 are turned OFF and switches S3 and S4 are turned ON. As a result, electric potential Vin is connected to a negative side of the condenser C1, electric potential Vin+Vin (2×Vin) is applied to a condenser C2, and electric charge that is charged into the condenser C1 is shifted to the condenser C2. As a result, an electric potential (3.1 V) that is double of Vin (1.55 V) is output as the Vout. The first and the second operation-steps are repeated.

Figure 7:
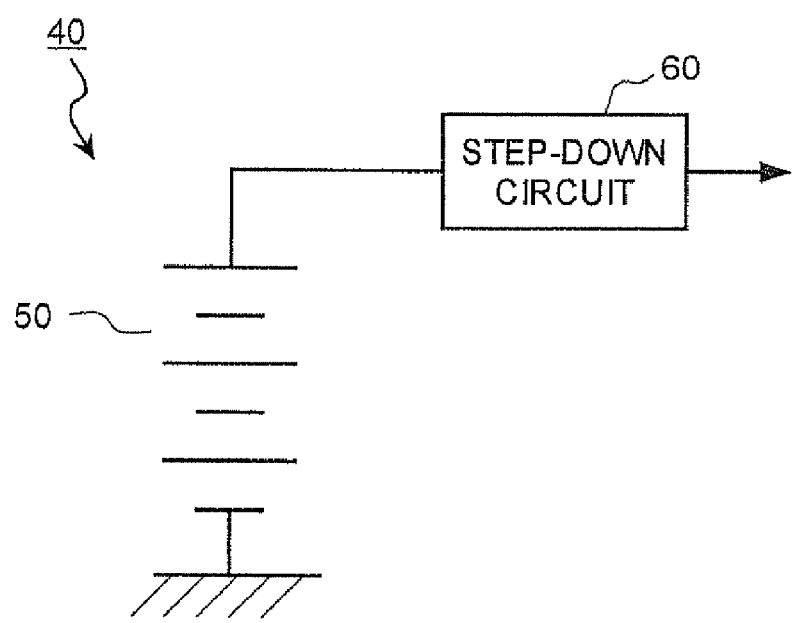
FIG. 7 is a circuit diagram of a power-supply circuit according to a second embodiment of the present invention.

FIG. 7 is a circuit diagram of a power-supply circuit 40 according to a second embodiment of the present invention. The power-supply circuit 40 includes a power-supply unit 50 and a step-down circuit 60. The power-supply circuit 40 includes four silver-oxide button cells connected in series. The silver-oxide button cells are the SR726SW cells.

The step-down circuit 60 steps down, to half, the voltage output from the power-supply unit 50. Thus, the current output from the step-down circuit 60 is double the current output from the power-supply unit 50. Concretely, since a current of 5 mA is required to be output from the step-down circuit 60, the power-supply unit 50 is made to output a current of 2.5 mA. Thus, lesser current is drawn from the cells in the second embodiment than those in the first embodiment, the cells in the second embodiment will last longer than those in the first embodiment. To surely output a voltage of 3.1 V from the power-supply circuit 40, four cells are required to be provided in the power-supply unit 50 so that a voltage of 6.2 V is output from the power-supply unit 50.

The step-down circuit 60 may be a step-down switching regulator circuit or a linear regulator. The step-down switching regulator circuit will now be explained while referring to FIGS. 8A and 8B.

The step-down switching regulator circuit is a power converting unit for achieving stable voltage and current output. The step-down switching regulator circuit includes a switch that is provided between an unstable power supply and a load. The power from the power supply is supplied to the load, or cut off by controlling ON/OFF of the switch. The power to be supplied can be adjusted on average by repeating the ON-OFF operation at a high speed, thereby stabilizing the voltage and the current. In the step-down switching regulator circuit, the switch and the load are connected in series. A low-power consumption DC-DC converter is used in the present embodiment.

Figure 8A:
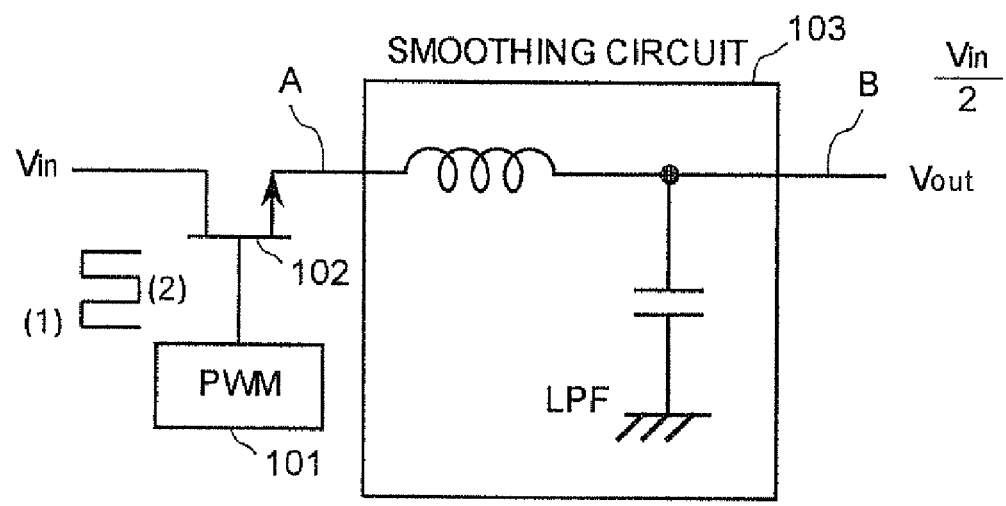
FIG. 8A is a circuit diagram of a step-down switching regulator circuit as an example of a step-down circuit in the power-supply circuit shown in FIG. 7.
Figure 8B:
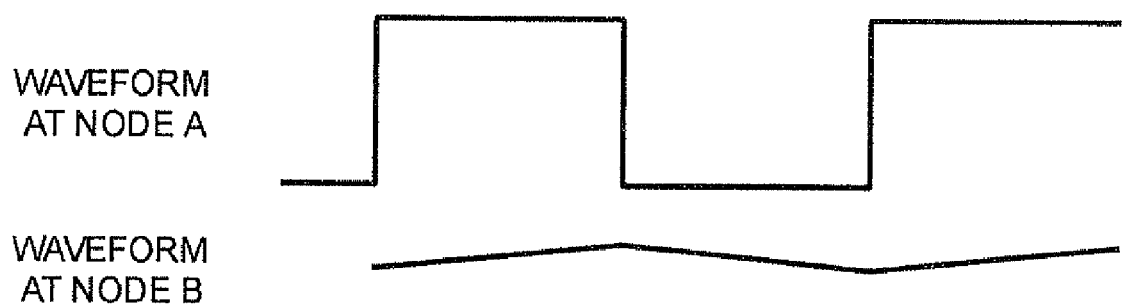
FIG. 8B is a waveform diagram of input and output of the step-down switching regulator circuit.

FIG. 8A is an exemplary circuit diagram of the step-down switching regulator circuit and FIG. 8B is a waveform diagram of an input and an output of the step-down switching regulator circuit.

Figure 9A:
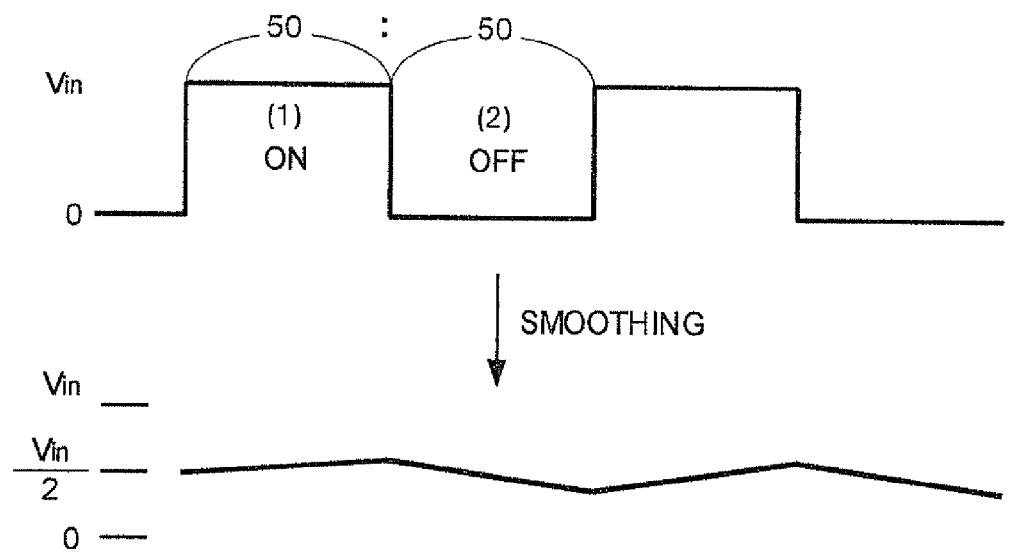
FIGS. 9A and 9B are waveform diagrams illustrating a relationship between electric potential at the node B and duty ratio of a clock generated at a PWM (pulse-width modulator) included in the step-down switching regulator circuit according to the second embodiment, where
Figure 9B:
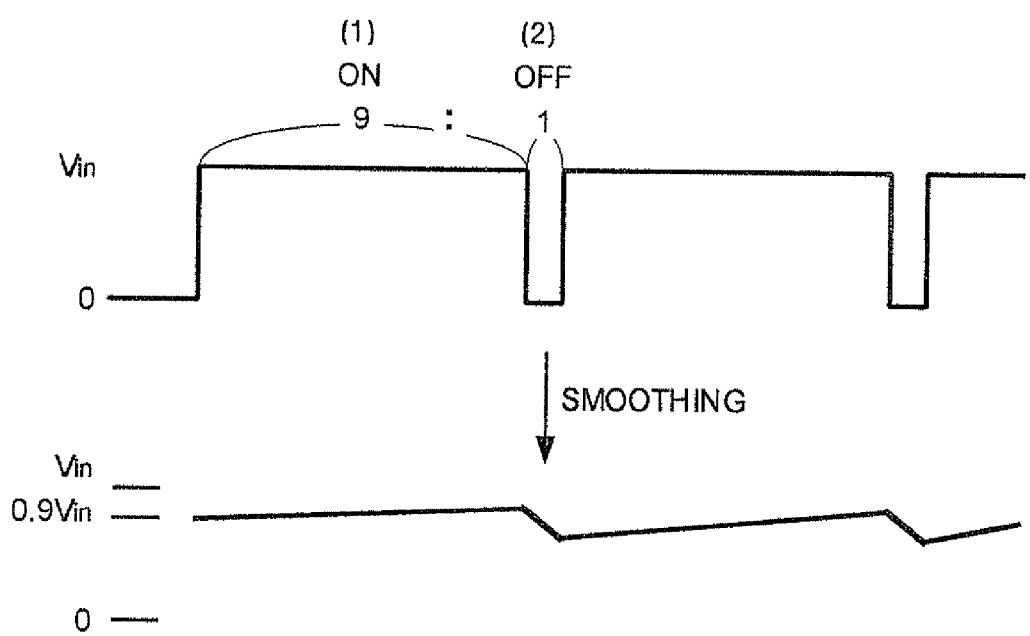

The step-down switching regulator circuit includes a pulse-width modulator (PWM) 101 that generate a clock by causing oscillation at a specific frequency, a transistor (for example, FET) 102 that is turned ON/OFF based on the clock, and a smoothing circuit 103. When the transistor 102 is turned ON, a node A, i.e., an input of the smoothing circuit 103, becomes an electric potential Vin and when the transistor is turned OFF, the node A becomes a high impedance (refer to FIG. 8B). The smoothing circuit 103 (for example, an LC or RC low-pass filter) performs smoothing of the node A. As a result, an electric potential of node B has a waveform shown in FIG. 8B. FIGS. 9A and 9B are waveform diagrams illustrating a relationship between the electric potential of the node B and a duty ratio of the clock generated in the PWM 101. As clear from FIG. 9A, when the duty ratio is 50%, the output voltage Vout (node B) becomes half of the input voltage Vin (used in the present embodiment). As clear from FIG. 9B, when the duty ratio is 90% for example, the output voltage Vout (node B) is 0.9 times of the input voltage Vin.

Figure 10A:
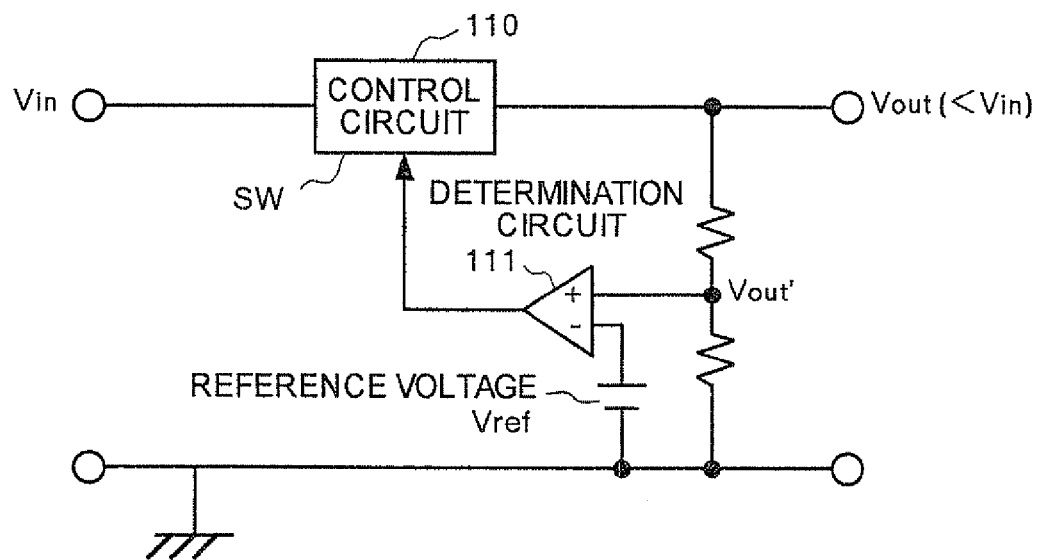
FIG. 10A is a circuit diagram of a linear regulator as an example of the step-down circuit and FIG. 10B is a waveform diagram illustrating a transistor operation and changes in the output voltage in FIG. 10A.
Figure 10B:
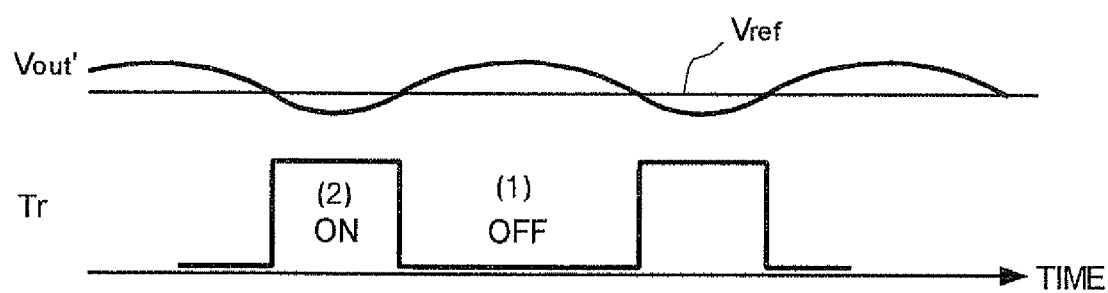

FIG. 10A is a circuit diagram of the linear regulator as an example of the step-down circuit 60 and FIG. 10B is a waveform diagram illustrating a transistor operation in a control circuit and changes in the output voltage.

The linear regulator includes a control circuit 110 that performs contractor control between a node on an input voltage Vin side and a node on an output voltage Vout side. The control circuit 110 is a transistor such as the FET. A determination circuit 111 is an operational amplifier. Reference voltage Vref is applied to a reverse-phase input terminal of the operational amplifier and voltage Vout' that is obtained by dividing the output volt Vout, is input to a normal-phase input terminal. The determination circuit 111 monitors the output voltage Vout and performs ON/OFF control of the transistor of the control circuit 110 based on a difference between the voltage Vout' and the reference voltage Vref. The reference voltage Vref is set to a value suitable for the desired voltage that is to be obtained as the output voltage Vout by stepping down the input voltage Vin.

If the voltage Vout' that corresponds to the output voltage Vout rises above that the reference voltage Vref, the transistor in the control circuit 110 is turned OFF (refer to (1) in FIG. 10B). If the voltage Vout' does not rise above the reference voltage Vref, the transistor in the control circuit 110 is turned ON (refer to (2) in FIG. 10B). As a result, the control is performed such that the voltage Vout' is the same as the reference voltage Vref (stabilization of the power supply) and the input voltage Vin is stepped down to the desired voltage.

Figure 11:
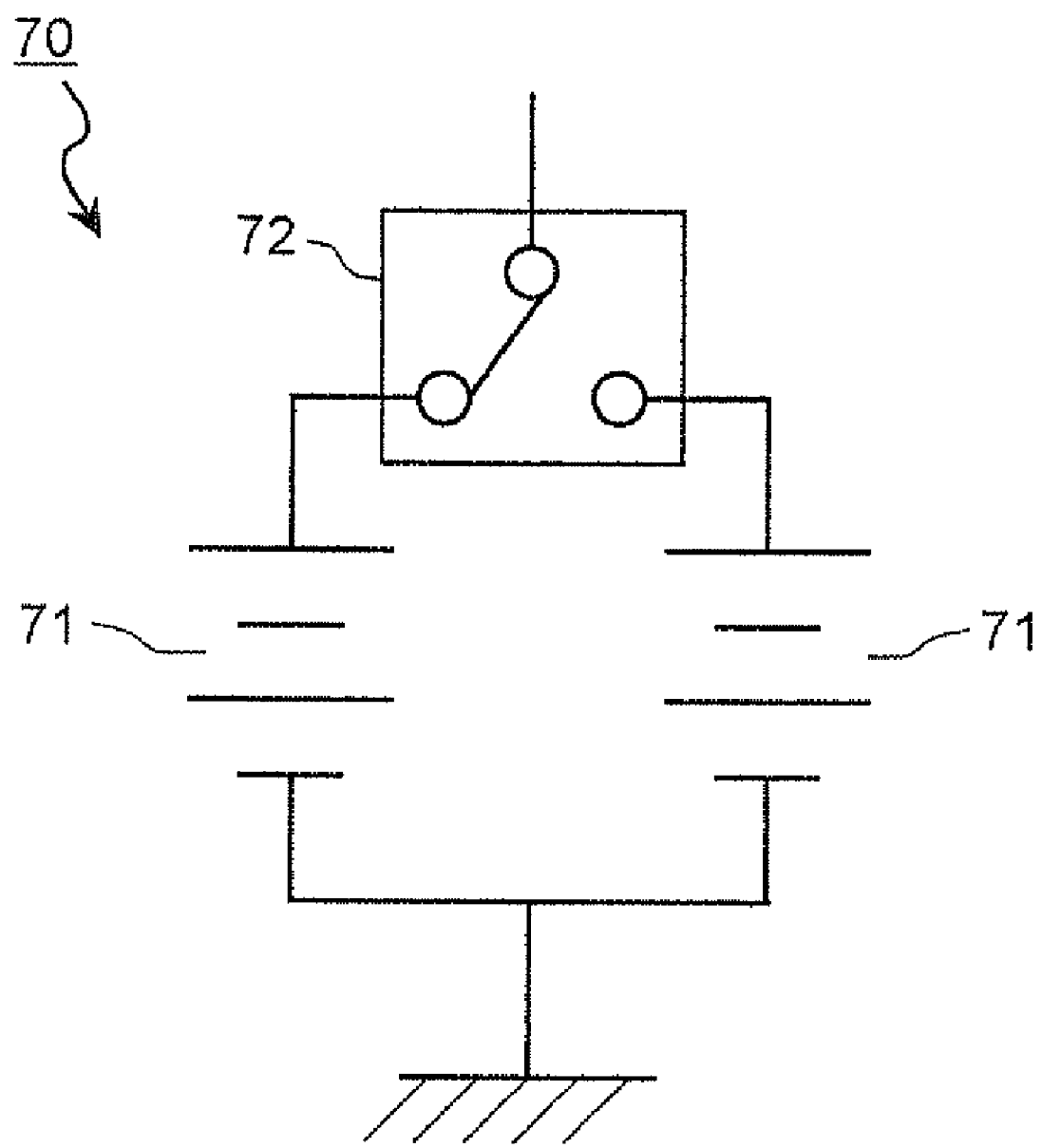
FIG. 11 is a circuit diagram of a power-supply circuit according to a third embodiment of the present invention.

FIG. 11 is a circuit diagram of a power-supply circuit 70 according to a third embodiment of the present invention. The power-supply circuit 70 includes two sets 71 of cells and a switch 72. Each set 71 includes two silver-oxide button cells connected in series. The switch 72 switches to any one of the sets 71. The SR726SW cells, which are the same as those used in the first and the second embodiments, are used as the silver-oxide button cells in the power-supply circuit 70. The step-up circuit or a step-down circuit is not required in the power-supply circuit 70. As a result, the number of components in the circuit is reduced.

Figure 12A:
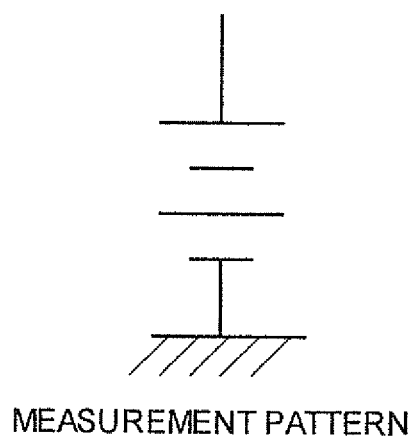
FIGS. 12A and 12B are illustrations of a measurement pattern and a result of an experiment about electrical discharge characteristics of a cell according to the third embodiment, where
Figure 12B:
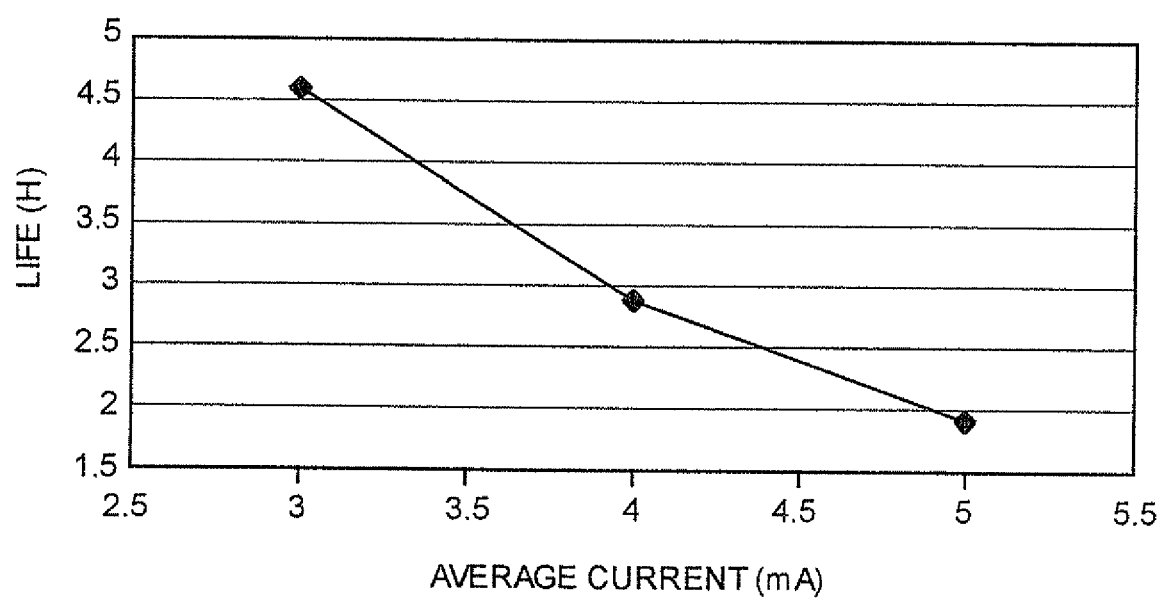

FIG. 12B is a graphical illustration of a result of an experiment about the electrical discharge characteristics of the silver-oxide button cells (SR726SW) in the power-supply circuit 70. FIG. 12A illustrates a measurement pattern and FIG. 12B illustrates the electrical discharge characteristics for the measurement pattern. In the in-body information acquiring apparatus according to the present embodiment, since an output of 3.1 V is required, the measurement pattern includes two silver-oxide button cells of 1.55 V connected in series (the measurement pattern is for one of the sets 71 in FIG. 11).

As shown in FIG. 12B, according to the electrical discharge characteristics of the silver-oxide button cells (measurement pattern) used in the third embodiment, the life of the cell is about two hours at an average current of 5 mA that is required for the in-body information acquiring apparatus according to the present embodiment. From the result of the experiment, when two measurement patterns are connected in parallel (i.e. instead of switching to any one of the two sets 71 as shown in FIG. 1 the two sets 71 are connected in parallel) the cell lasts for about four hours at an average current of 5 mA.

Whereas, according to the third embodiment, the two sets 71 are used while switching to any one of the two sets by the switch 72. The switch 72 is made to switch every 7 to 8 minutes. It was discovered by an experiment that in this case the cell lasts for seven to eight hours. Thus, it was discovered that when the sets 71 are switched by the switch 72, the life of the cell is 1.5 to 2 times more than that in the case when the cells are connected in parallel without switching (a value based on the experiment result shown in FIG. 12B: about four hours). This is due to a temporary revival of a capability resulted from not using the cell by disconnecting it due to switching. By using such an arrangement, it is possible to provide the power-supply circuit that fulfils the requirements of the voltage, current, and life of the cell required for the in-body information acquiring apparatus according to the present embodiment, at low cost by using easily procurable cells available in the market.

Thus, the power-supply circuit of the present invention provides an output that is suitable for the in-body information acquiring apparatus and uses cells that are available in the market. Thus, the in-body information acquiring apparatus can be made compact and can be manufactured at a lower cost.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:
1. A swallowable capsule endoscope comprising;
a swallowable case configured to be introduced into a patient;
a function executing unit configured to realize a predetermined function inside the patient when the swallowable case travels inside the patient, the function executing unit being accommodated in the case;
a plurality of silver-oxide button cells accommodated in the swallowable case each of the plurality of silver-oxide button cells having a diameter less than 10 mm; and
a converter configured to convert an output voltage output from the plurality of silver-oxide button cells to an operational voltage required to operate the function executing unit, wherein
the converter includes a step-up converter that steps-up the output voltage of the plurality of silver-oxide button cells to the operational voltage higher than the output voltage when the plurality of silver-oxide button cells are electrically connected in parallel or a step-down converter that steps-down the output voltage of the plurality of silver-oxide button cells to the operational voltage lower than the output voltage when the plurality of silver-oxide button cells are electrically connected in series.

2. The swallowable capsule endoscope according to claim 1, wherein the step-up converter is a charge pump.

3. The swallowable capsule endoscope according to claim 1, wherein the step-down converter is a step-down switching regulator circuit.

4. The swallowable capsule endoscope according to claim 1, wherein the step-up converter is a linear regulator.

5. The swallowable capsule endoscope according to claim 1, wherein the cell is a SR726SW cell.

6. The swallowable capsule endoscope according to claim 1, wherein the step-up converter is a step-up switching regulator circuit.

* * * * *